United States Patent [19]

Hara et al.

[11] Patent Number: 4,906,782
[45] Date of Patent: Mar. 6, 1990

[54] PROCESS FOR PREPARATION OF ALKYLENEAMINES

[75] Inventors: Yasushi Hara, Shinnanyo; Sadakatsu Kumoi, Hikari; Yukihiro Tsutsumi, Kawasaki, all of Japan

[73] Assignee: Toyo Soda Manufacturing Co., Ltd., Shinnanyo, Japan

[21] Appl. No.: 84,558

[22] Filed: Aug. 12, 1987

[30] Foreign Application Priority Data

Aug. 13, 1986 [JP] Japan ................. 61-188664

[51] Int. Cl.$^4$ .............................................. C07C 85/06
[52] U.S. Cl. .................... 564/478; 540/470; 540/484; 540/553; 540/575; 544/358; 544/402; 544/410
[58] Field of Search ........... 564/479, 478, 479; 544/358, 402, 335, 410; 540/470, 553, 575, 484

[56] References Cited

U.S. PATENT DOCUMENTS

| | | | |
|---|---|---|---|
| 2,813,869 | 11/1957 | Langdon | 544/336 |
| 3,714,259 | 1/1973 | Lichtenwalter et al. | 544/358 |
| 4,049,657 | 9/1977 | Brennan et al. | 544/402 |
| 4,289,656 | 9/1981 | Hayes et al. | 548/969 |
| 4,376,732 | 3/1983 | Ramirez | 548/969 |
| 4,394,524 | 7/1983 | Ford et al. | 564/479 |
| 4,448,997 | 5/1984 | Brennan et al. | 564/479 |
| 4,578,517 | 3/1986 | Johnson et al. | 564/479 |
| 4,698,427 | 10/1987 | Vanderpool | 564/509 |

OTHER PUBLICATIONS

Hoshiai, CA 80-136999s (1974).
Brennan et al., CA 87-5367f (1977).
Anderpool et al., CA 101-194142y (1984).
Johnson et al., CA 101-170696c (1984).
Brennan et al., CA 105-42324a.

Primary Examiner—Mukund J. Shah
Assistant Examiner—Cecilia Shen
Attorney, Agent, or Firm—Cushman, Darby & Cushman

[57] ABSTRACT

Ammonia and/or an alkyleneamine is reacted with an alkanolamine by using a miobium-containing substance as a catalyst to obtain an alkyleneamine having an increased number of alkylene units. The niobium-containing substance has a high activity and a high heat resistance, and is not or only slightly soluble in the water-containing reaction liquid.

9 Claims, No Drawings

PROCESS FOR PREPARATION OF ALKYLENEAMINES

BACKGROUND OF THE INVENTION (1) Field of the Invention

The present invention relates to a process for the preparation of alkyleneamines. More particularly, it relates to a process for preparing an alkyleneamine by using a niobium-containing substance as a catalyst.

(2) Description of the Related Art

As means for preparing alkyleneamines, especially ethyleneamines which are industrially important, there can be mentioned a process in which ethylene dichloride is reacted with ammonia. According to this process, amounts formed of piperazine and a piperazine ring-containing cyclic ethyleneamine are small, that is, the non-cyclic ratio is high, and an ethyleneamine having an industrially preferable quality can be obtained. Accordingly, this process is widely carried out. However, in this process, a large quantity of sodium chloride is formed as a by-product and expenses are necessary for separation and treatment of this sodium chloride.

Furthermore, a process for preparing an ethyleneamine by reacting monoethanolamine as the starting material with ammonia in the presence of hydrogen and a hydrogenation catalyst is widely worked. Although ethylenediamine can be efficiently prepared according to this process, since a large quantity of a piperazine ring-containing cyclic ethyleneamine, which is not preferred from the viewpoint of quality, is inevitably formed, it is difficult to obtain a polyethylene-polyamine having a high molecular weight.

U.S. Pat. No. 3,714,259 proposes a process in which a polyethylene-polyamine is prepared by carrying out the liquid phase reaction between ethylenediamine and ethanolamine in the presence of a hydrogenation catalyst such as Ni, Cu or Cr in a hydrogen gas atmosphere. According to this process, only a lower polyethylene-polyamine such as diethylenetriamine is formed and a higher polyethylene-polyamine such as tetraethylenepentamine or pentaethylenehexamine cannot be obtained. Furthermore, if the reaction is carried out under conditions where the conversion of the starting compound is sufficiently increased, the amount formed of a cyclic polyethylene-polyamine which is not preferred in view of quality, such as piperazine or aminoethylpiperazine, is increased, and a polyamine compound having a hydroxyl group in the molecule is formed.

In addition to the foregoing processes, there is proposed a process for preparing ethyleneamines by reacting monoethanolamine in the presence of a phosphorus-containing substance as the catalyst. For example, Japanese Unexamined Patent Publication No. 51-147,600 discloses a process using phosphoric acid or phosphorous acid as the catalyst. However, since the catalyst of this type is dissolved in a reaction liquid containing water, a special operation is necessary for separating and recovering the catalyst. As means for eliminating this disadvantage, a process using a phosphate or supported phosphoric acid as a catalyst, which is insoluble in a reaction liquid containing water, is proposed. For example, U.S. Pat. No. 4,448,997 teaches a process for the preparation of ethyleneamines where aluminum phosphate is used as a catalyst, and Japanese Unexamined Patent Publication No. 60-41,641, which corresponds to U.S. Pat. No. 4,463,193 discloses a process for preparing ethyleneamines where a phosphoric acid salt of a metal of the group IIIb such as lanthanum phosphate is used as a catalyst. Furthermore, Japanese Unexamined Patent Publication No. 59-150,538, which corresponds to U.S. Pat. No. 4,640,822, discloses a process using as a catalyst phosphoric acid supported on titanium dioxide or the like. However, these phosphate and supported phosphoric acid catalysts have an activity lower than free phosphoric acid and it is impossible to prepare a polyethylene-polyamine efficiently. Moreover, when the phosphate or supported phosphoric acid catalyst is used, it is impossible to reduce the content of a piperazine ring-containing cyclic amine which is not preferred from the viewpoint of quality or a hydroxyl group-containing amine such as aminoethylethanolamine to an industrially satisfactory level.

As means for overcoming the defects of these phosphorus-containing catalysts, there can be mentioned a process using a phosphorus-containing ion exchange resin as a phosphorus catalyst having an enhanced activity, as disclosed in Japanese Unexamined Patent Publication No. 57-74,331. However, this catalyst has poor heat resistance and catalyst life.

Silica-alumina catalysts are disclosed in Japanese Unexamined Patent Publication No. 55-38,329 and Japanese Unexamined Patent Publication No. 60-156,651, which corresponds to U.S. Pat. No. 4,547,591 as non-phosphorus catalysts, but these catalysts have extremely low activity. Accordingly, in the latter patent publication, phosphoric acid is added as an assistant to increase the catalyst activity.

Various processes for preparing alkyleneamines have been proposed as pointed out hereinbefore, but these processes have the following problems.

(1) In the case of a liquid catalyst, the operation of separating and recovering the catalyst from a formed polyamine after termination of the reaction is necessary, and this operation is complicated and a separating equipment is necessary. Accordingly, a solid catalyst is preferred from the industrial viewpoint.

(2) Solid catalysts proposed in the past have a poor activity. Furthermore, in the presence of water, partial decomposition is caused at high temperatures and the activity is degraded with the lapse of time.

(3) In the case of a phosphorus type supported solid catalyst, when active sites are exposed to high temperatures in the presence of water, they are liable to separate from the surface of the carrier. Accordingly, the activity is reduced with the lapse of time and in order to maintain the reactivity, it is necessary to elevate the reaction temperature extremely. This leads to an increase of the reaction pressure.

Especially, in a process for preparing alkyleneamines from alkanolamines as the starting substance, development of a technique of preparing an alkyleneamine having a high non-cyclic ratio and a high quality by using a solid catalyst having a high activity and a high heat resistance, which is not or only slightly soluble in a reaction liquid, is eagerly desired.

SUMMARY OF THE INVENTION

In view of the foregoing, it is a primary object of the present invention to provide a process for an alkyleneamine having an increased number of alkylene units wherein ammonia and/or an alkyleneamine is reacted with an alkanolamine by using a solid catalyst which has a high activity and a high heat resistance and is not or only slightly soluble in the water-containing reaction liquid.

In accordance with the present invention, there is provided a process for preparing an alkyleneamine having an increased number of alkylene units from a starting material selected from the group consisting of ammonia and alkyleneamines, the starting material is reacted with an alkanolamine in the presence of a niobium-containing substance.

DESCRIPTION OF THE PREFERRED EMBODIMENTS

The present invention will now be described in detail.

The catalyst used in the process of the present invention is a niobium-containing substance, by which is meant a substance in which niobium is chemically bonded to other element. Any of niobium-containing substances can be used without any limitation. As specific examples of the niobium-containing substance, there can be mentioned niobium oxides such as niobium pentoxide, niobium tetraoxide, niobium trioxide, niobium dioxide and niobium monoxide; niobic acid salts such as lithium niobate, sodium niobate, magnesium niobate, aluminum niobate, potassium niobate, calcium niobate, manganese niobate, iron niobate, rubidium niobate, yttrium niobate, silver niobate, lead niobate, cesium niobate, barium niobate and mercury niobate; fluoroniobic acid salts such as sodium fluoroniobate and potassium fluoroniobated; niobium fluorides such as niobium pentafluoride and niobium trifluoride; niobium chlorides such as niobium pentachloride, niobium tetrachloride and niobium trichloride; niobium bromides such as niobium pentabromide, niobium tetrabromide and niobium tribromide; niobium iodides such as niobium pentaiodide, niobium tetraiodide and niobium triiodide; niobium oxyhalides such as niobium oxyfluoride, niobium oxychloride, niobium oxybromide and niobium oxyiodide; niobium alkoxides such as niobium methoxide, niobium ethoxide, niobium propoxide, niobium isopropoxide, niobium butoxide, niobium pentyloxide and niobium phenoxide; and organic acid salts of niobium such as niobium oxalate. A substance in which pentavalent niobium is chemically bonded to other element is preferred as the catalyst used in the present invention, and niobium oxides and niobic acid salts are further preferred.

In the process of the present invention, the form of pentavalent niobium oxide is not particularly critical, and either an anhydride or a hydrate can be used. Hydrous niobium pentoxide is called niobic acid and is generally expressed as $Nb_2O_5 \cdot xH_2O$ ($0 < x \leq 5$). In the case of $x=5$, the niobium oxide is called niobium hydroxide. The pentavalent niobic acid salt includes an ortho-niobic acid salt and a meta-niobic acid salt and each of them can be used as the catalyst. However, the ortho-niobic acid salt, which is almost insoluble, is preferred. In the process of the present invention, pentavalent niobium oxides and pentavalent niobic acid salts can be used singly in the form of mixtures of two or more of them.

The process for preparing the niobium-containing substance is not particularly critical. For example, in the case of niobium pentoxide, there can be mentioned (1) a process in which a niobic acid salt, a fluoroniobic acid salt, a niobium halide or a niobium alkoxide is hydrolyzed, (2) a process in which a niobium alkoxide or an organic acid salt of niobium is thermally decomposed, and (3) a process in which a natural ore is dissolved by hydrofluoric acid and is then extracted. Any preparing process can be adopted without any limitation.

In the process of the present invention, the pentavalent niobium oxide or pentavalent niobic acid salt can be used singly as the catalyst or in the form of a mixed oxide catalyst with an oxide of other element. For example, a mixed oxide comprising niobium pentoxide and silica, alumina, titania or zirconia can be mentioned.

In the process of the present invention, the shape of the catalyst is not particularly critical. The catalyst can be used in the powdery state or in the form of a molded article according to the reaction mode. For example, the catalyst is used in the form of a powder or granule in a suspended bed or is used in the form of a molded pellet or bead in a fixed bed.

As the catalyst-molding method, there can be mentioned an extrusion molding method, a tableting method and a granulation method. At the molding step, silica, alumina, silica-alumina or clay may be added as a binder.

In order to increase the surface area of the catalyst, the niobium-containing substance may be supported on a carrier such as silica gel, alumina, titania, zirconia or porous Vycor glass.

The catalyst may be used after calcination or without calcination. When the catalyst is calcined, the calcination temperature is not particularly critical. However, in the case of niobium pentoxide, the calcination temperature is preferably not higher than 500° C. If niobium pentoxide is calcined at a temperature exceeding 500° C., crystallization is caused and the catalyst activity is reduced.

In the process of the present invention, it is sufficient if the amount of the niobium-containing substance used as the catalyst is an amount necessary for advancing the reaction at an industrially significant speed. Since the amount of the catalyst used greatly differs according to whether the reaction is of the suspended bed type or the fixed bed type, it is difficult to specify the amount of the catalyst used. For example, in the case of the suspended bed, the catalyst is generally used in an amount of 0.05 to 50% by weight based on the total amount of the starting materials. If the amount of the catalyst is smaller than 0.05% by weight, a sufficient rate of reaction cannot be obtained, and if the amount of the catalyst exceeds 50% by weight, no substantial effect can be attained by increase of the amount of the catalyst.

In the process of the present invention, ammonia and/or alkyleneamines, and alkanolamines are used as the starting materials.

The ammonia and alkyleneamines used as a starting compound in the process of the present invention are compounds represented by the following formula (I):

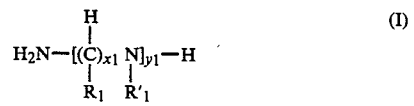

wherein $x_1$ is a number of from 2 to 6, $y_1$ is a number of from 1 to 6, $R_1$ represents a hydrogen atom or an alkyl group having 1 to 4 carbon atoms, and $R'_1$ represents a group represented by the following formula (1):

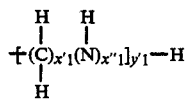

wherein $x'_1$ is a number of from 1 to 6, $x''_1$ is 0 or 1 and $y'_1$ is a number of from 0 to 4, or compounds represented by the following formula (II):

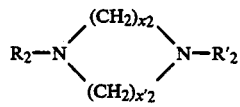

wherein $x_2$ and $x'_2$ are numbers of from 2 to 6, and $R_2$ and $R'_2$ represent a group represented by the following formula (2):

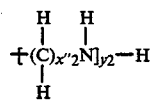

wherein $x''_2$ is a number of from 2 to 6 and $y_2$ is a number of from 0 to 5.

Either a starting compound represented by the formula (I) or a starting compound represented by the formula (II) can be used. However, ammonia or an alkyleneamine represented by the formula (I) is preferably used. If an alkyleneamine represented by the formula (I) is used, an alkyleneamine having a high non-cyclic ratio and a high quality is formed. As specific examples of the starting compound represented by the formula (I), there can be mentioned ammonia; ethyleneamines such as ethylenediamine, diethylenetriamine, triethylenetetramine, tetraethylenepentamine, pentaethylenehexamine and hexaethyleneheptamine; propyleneamines such as propylenediamine, dipropylenetriamine and tripropylenetetramine; butyleneamines such as butylenediamine and dibutylenetriamine; alkyleneamines such as hexamethylenediamine; and alkylation products thereof such as N-methylethylenediamine and N-ethylethylenediamine. Among the foregoing compounds, an ethyleneamine such as ethylenediamine or diethylenetriamine or a propyleneamine such as 1,3-propylenediamine is preferably used as the stating material in the process of the present invention.

In the process of the present invention, ammonia and alkyleneamines can be used singly or in the form of mixtures of two or more of them.

Alkanolamines used in the present invention are compounds represented by the following formula (III):

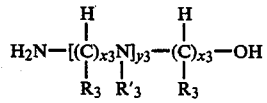

wherein $x_3$ is a number of from 2 to 6, $y_3$ is a number of from 0 to 5, $R_3$ represents a hydrogen atom or an alkyl group having 1 to 4 carbon atoms, and $R'_3$ is a group represented by the following formula (3):

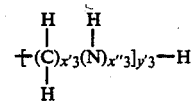

wherein $x'_3$ is a number of from 1 to 6, $x''_3$ is 0 or 1 and $y'_3$ is a number of from 0 to 4, or compounds represented by the following formula (IV):

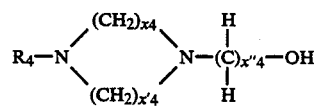

wherein $x_4$, $x'_4$ and $x''_4$ are numbers of from 2 to 6 and $R_4$ represents a group represented by the following formula (4):

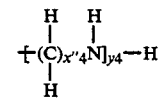

wherein $x''_4$ is a number of from 2 to 6 and $y_4$ is a number of from 0 to 4.

Either a compound represented by the formula (III) or a compound represented by the formula (IV) can be used, but an alkanolamine represented by the formula (III) is preferably used. If an alkanolamine represented by the formula (III) is used, an alkyleneamine having a high non-cyclic ratio and a high quality is formed. As specific examples of the alkanolamine represented by the formula (III), there can be mentioned monoethanolamine, N-(2-aminoethyl)ethanolamine, ]{N'-(2-aminoethyl)}-N-(2-aminoethyl)[-ethanolamine, monopropanolamine, propanol isomers thereof, N-(3-aminopropyl)propanolamine and N-(2-aminopropyl)-1,2-propanolamine.

An ethanolamine such as monoethanolamine or N-(2-aminoethyl)ethanolamine or a propanolamine such as 3-amino-1-propanol is preferably used as the starting material in the process of the present invention.

In the process of the present invention, the alkanolamines may be used singly or in the form of mixtures of two or more of them.

As the combination of the starting materials used for the reaction in the process of the present invention, the following combination can be mentioned: (1) ammonia and an alkanolamine, (2) an alkyleneamine and an alkanolamine, and (3) ammonia, an alkyleneamine and an alkanolamine. Any of the foregoing combinations can be used for the reaction. Preferred combinations of the starting materials are (1) a combination of ammonia and an alkanolamine represented by the formula (III), (2) a combination of an alkyleneamine represented by the formula (I) other than ammonia and an alkanolamine represented by the formula (III), and (3) ammonia, an alkyleneamine represented by the formula (I) and an alkanolamine represented by the formula (III). Especially preferred combinations of the starting materials are (1) a combination of ammonia and an ethanolamine, (2) a combination of an ethyleneamine and an ethanolamine, and (3) a combination of ammonia, an ethyleneamine and an ethanolamine.

Preferred molar ratios of the starting materials supplied in the process of the present invention are described below. In the case (1) where ammonia and an alkanolamine are used as the starting materials, the ammonia/alkanolamine molar ratio is preferably from 2 to 30. In the case (2) where an alkyleneamine and an alkanolamine are used as the starting materials, the alkyleneamine/alkanolamine molar ratio is preferably from 0.5 to 10. In the case (3) where ammonia, an alkyleneamine and an alkanolamine are used as the starting materials, the (ammonia plus alkyleneamine)/alkanolamine molar ratio is preferably from 0.5 to 30. In each case, the quality of the formed alkyleneamine is changed according to the molar ratio of the starting materials. If the molar ratio is too low and below the above-mentioned range, a large amount of a piperazine ring-containing amine is formed and the quality of the formed alkyleneamine is not good. If the molar ratio is too high and exceeds the above-mentioned range, the rate of reaction is lowered and the pressure becomes extremely high, and too high a molar ratio is not preferred from the practical viewpoint.

In the process of the present invention, the kind of the formed alkyleneamine differs according to the kinds of the starting materials. In the case where ammonia and/or an alkyleneamine is reacted with an alkanolamine, the formed alkyleneamine is an alkyleneamine in which the number of alkylene units is increased over that in the starting ammonia and/or alkyleneamine. For example, in the case where ammonia or an alkyleneamine represented by the formula (I) is reacted with an alkanolamine represented by the formula (III), the formed alkyleneamine is a compound represented by the following formula (V):

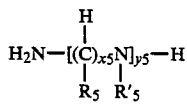
(V)

wherein $x_5$ is a number of from 2 to 6, $y_5$ is a number of from 1 to 7, $R_5$ represents a hydrogen atom or an alkyl group having 1 to 4 carbon atoms, and $R'_5$ represents a group represented by, the following formula (5):

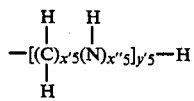
(5)

wherein $x'_5$ is a number of from 1 to 6, $x''_5$ is 0 or and $y'_5$ is a number of from 0 to 4. In the formed alkyleneamine represented by the formula (V) or formula (5), $y_5$ or $y'_5$ is a number larger by at least 1 than $y_1$ or $y'_1$ in the starting ammonia or alkyleneamine represented by the formula (I) or (1). More specifically, if ammonia is reacted with monoethanolamine, ethylenediamine and non-cyclic polyethylene-polyamines such as diethylenetriamine, triethylenetetramine, tetraethylenepentamine and pentaethylenehexamine are formed. If ethylenediamine is reacted with monoethanolamine, non-cyclic polyethylenepolyamines are formed, and if ammonia and ethylenediamine are reacted with monoethanolamine, non-cyclic polyethylene-polyamines are formed.

Furthermore, if ammonia and/or propylenediamine is reacted with propanolamine, polypropylene-polyamines such as dipropylenetriamine, tripropylenetetramine, tetrapropylenepentamine and pentapropylenehexamine are formed.

In the process of the present invention, the reaction is generally carried out at 200° to 400° C., preferably 240° to 350° C. If the reaction temperature is lower than 200° C., the rate of reaction is drastically reduced, and if the reaction temperature is higher than 400° C., decomposition of the formed alkyleneamine is caused and too high a reaction temperature is not preferred from the practical viewpoint.

In the process of the present invention, the reaction pressure is greatly varied according to whether the reaction is a gas phase reaction or a liquid phase reaction, or whether ammonia is used or not used, and it is difficult to specify the range of the reaction pressure, but in the liquid phase reaction not using ammonia, the reaction pressure is about 1 to about 300 kg/cm² G.

In the process of the present invention, the reaction may be carried out in the gas phase or in the liquid phase, but in order to obtain an alkyleneamine having a high quality, the reaction is preferably carried out in the liquid phase.

In the process of the present invention, the reaction may be carried out batchwise, semi-batchwise or in a continuous manner, or the reaction may be carried out in a flowing manner in a fixed bed. Industrially, the flowing reaction in a fixed bed is preferred in view of the operation and apparatus and from the practical viewpoint. For example, in the case of a flowing continuous reaction in a fixed bed, a catalyst molded in a pellet is packed in a fixed bed reactor and starting materials are continuously supplied. The reaction is carried out under a pressure sufficient to maintain a liquid phase. In general, the reaction temperature is selected so that the residence time of the reaction liquid is 0.2 to 5 hours.

In the process of the present invention, the catalyst is generally recovered from the reaction liquid and is used again, and the starting materials are recovered by distillation. The recovered starting materials are recycled to the reaction zone according to need. In order to change the composition of the reaction product, a part of the reaction product may be recycled into the reaction zone. The separation of the starting materials and reaction product can be performed by distillation, and the distillation may be carried out in a continuous manner or batchwise. In order to improve the purity and hue of the reaction product, the reaction product may be treated with active carbon, sodium boron hydride or the like. Moreover, the hue and smell can be improved by carrying out the reaction in the presence of hydrogen. In order to control formation of an amine which is not preferred in view of the quality, such as a hydroxyl group-containing amine or elevate the rate of reaction, water formed by the reaction may be removed from the reaction zone. In order to prolong the life of the catalyst and facilitate the handling of ammonia and alkyleneamines, the reaction may be carried out while adding water.

According to the present invention, by using a niobium-containing substance, which has a high catalytic activity, is not affected by the reaction liquid and has an excellent heat resistance, as a catalyst, alkyleneamines having a desired quality can be obtained while highly controlling formation of piperazine, aminoethylpiperazine, hydroxyethylpiperazine and high polyethylenepolyamines containing a piperazine ring. Furthermore, amounts of hydroxyl group-containing alkyleneamines formed can be controlled.

Moreover, the catalyst used in the present invention is not eluted into the formed alkyleneamine.

The present invention will now be described in detail with reference to the following examples that by no means limit the scope of the invention.

For simplifying the description, the following abbreviations are used for formed alkyleneamines and starting ammonia, alkyleneamines and alkanolamines.

EDA: ethylenediamine
MEA: monoethanolamine
PIP: piperazine
AEP: N-(2-aminoethyl)piperazine
HEP: N-(2-hydroxyethyl)piperazine
DETA: diethylenetriamine
AEEA: N-(2-aminoethyl)ethanolamine
TETA: triethylenetetramine (linear, branched and cyclic isomers)
TEPA: tetraethylenepentamine (linear, branched and cyclic isomers)
PEHA: pentaethylenehexamine (linear, branched and cyclic isomers)
NH₃: ammonia In tables in examples given hereinafter, the amount (% by weight) of the reaction product is the amount obtained by subtracting amounts of the starting materials, low-boiling-point substances, NH₃ and formed water from the amount of the reaction mixture.

The TETA non-cyclic percentage is a gaschromatogram area percentage of TETA free of a piperazine ring and is expressed by

[(branched and linear isomers)/(branched, linear and cyclic isomers)] × 100.

The hydroxyl group content (%) is the content (% by weight) of the hydroxyl group-containing amine and is expressed by [AEEA/(AEEA+DETA)] × 100.

EXAMPLES 1 THROUGH 5 AND COMPARATIVE EXAMPLES 1 THROUGH 5

A stainless steel autoclave equipped with an electromagnetic stirrer and having a capacity of 300 ml was charged with 90 g of EDA, 45 g of MEA and a catalyst shown in Table 1. The temperature of the charged starting material mixture was elevated to 300° or 250° C. and the reaction was carried out at this temperature for 3 to 5 hours. After termination of the reaction, the reaction liquid was cooled and the composition of the reaction liquid was analyzed by the gas chromatography. The results are shown in Table 1.

Niobium pentoxide used in Examples 1 through 5 was obtained by heat-treating niobium pentoxide supplied by CBMM Co. at 100° C. for 16 hours and pulverizing the heat-treated product. This niobium pentoxide contained 84.6% by weight of Nb₂O₅ and 14.2% by weight of an ignition loss (700° C.). Lanthanum phosphate used in the Comparative Examples was prepared according to the process for the synthesis of catalyst A disclosed in Japanese Unexamined Patent Publication No. 60-41,641 and aluminum phosphate used in Comparative Examples was prepared according to the synthesis process disclosed in the specification of U.S. Patent No. 4,448,997. Silica-alumina was supplied by Davison Co.

TABLE 1

| | | Catalyst | Amount of catalyst (g) | Reaction temperature (°C.) | Reaction time (hrs) | Conversion of MEA (%) | Reaction products (% by weight) | | | | | | | |
|---|---|---|---|---|---|---|---|---|---|---|---|---|---|---|
| | | | | | | | PIP | DETA | AEEA | AEP | HEP | TETA | TEPA | PEHA |
| Example | 1 | Niobium pentoxide | 1.4 | 300 | 5.0 | 48 | 2.3 | 59.8 | 2.6 | 1.0 | 0.0 | 15.0 | 2.0 | 1.0 |
| " | 2 | Niobium pentoxide | 2.7 | 300 | 3.0 | 50 | 2.3 | 57.9 | 1.8 | 1.3 | 0.0 | 15.3 | 2.0 | 1.1 |
| " | 3 | Niobium pentoxide | 2.7 | 300 | 3.0 | 64 | 3.3 | 52.9 | 0.1 | 2.5 | 0.0 | 18.6 | 3.5 | 1.2 |
| " | 4 | Niobium pentoxide | 4.1 | 300 | 5.0 | 74 | 5.7 | 48.0 | 0.2 | 4.4 | 0.0 | 21.1 | 5.7 | 2.0 |
| " | 5 | Niobium pentoxide | 4.1 | 250 | 5.0 | 7 | 1.0 | 82.1 | 8.9 | 0.3 | 0.0 | 1.0 | — | — |
| Comparative Example | 1 | Lanthanum phosphate | 4.1 | 300 | 3.0 | 27 | 1.8 | 65.0 | 20.7 | 0.0 | 0.0 | 4.2 | 0.0 | 0 |
| Comparative Example | 2 | Aluminum phosphate | 4.1 | 300 | 3.0 | 30 | 2.5 | 71.1 | 19.5 | 1.1 | 0.1 | 2.2 | 0.0 | 0 |
| Comparative Example | 3 | Silica-alumina | 4.1 | 300 | 5.0 | 5 | 0.1 | 76.0 | 23.8 | 0.0 | 0.0 | 0.0 | 0.0 | 0 |
| Comparative Example | 4 | Aluminum phosphate | 4.1 | 250 | 5.0 | 0 | — | — | — | — | — | — | — | — |
| Comparative Example | 5 | Lanthanum phosphate | 4.1 | 250 | 5.0 | 0 | — | — | — | — | — | — | — | — |

EXAMPLES 6 THROUGH 11 AND COMPARATIVE EXAMPLES 6 THROUGH 8

A stainless steel autoclave equipped with an electromagnetic stirrer and having a capacity of 200 ml was charged with 60 g of EDA, 30 g of MEA and a catalyst shown in Table 2. The temperature of the charged starting material mixture was elevated to 300° C. and this temperature was maintained for a time shown in Table 2 to effect reaction. After termination of the reaction, the composition of the reaction liquid was analyzed by the gas chromatography. The results are shown in Table 2. In the Examples, the catalyst recovery ratio was 100%.

Niobium pentoxide (supplied by CBMM Co.) used in Examples 6 through 8 was calcined at 400° C. for 2 hours in dry air, niobium pentoxide (supplied by CBMM Co.) used in Example 9 was calcined at 200° C. for 2 hours in dry air, and niobium pentoxide used in Example 10 was obtained by hydrolyzing niobium pentachloride, washing the hydrolysis product with water and calcining the washed hydrolysis product at 400° C.

for 2 hours in dry air. Aluminum phosphate and lanthanum phosphate used in the Comparative Examples are the same as those used in Comparative Examples 2 and 1, respectively. Silica was supplied by Nikki Chemical Co.

the conversion of MEA was calculated. The results are shown in Table 4.

In Comparative Example 9, the reaction was carried out by adding 3.0 g of the same lanthanum phosphate as used in Comparative Example 1.

TABLE 2

| | | Catalyst | Amount of catalyst (g) | Reaction time (hrs) | Conversion of MEA (%) | Reaction products (% by weight) | | | | | | | TETA non-cyclic percentage (%) | Hydroxyl group content (%) |
|---|---|---|---|---|---|---|---|---|---|---|---|---|---|---|
| | | | | | | PIP | DETA | AEEA | AEP | HEP | TETA | TEPA | | |
| Example | 6 | Niobium pentoxide | 1.0 | 3.0 | 47.1 | 3.3 | 66.2 | 0.3 | 1.7 | 0.0 | 15.5 | 1.0 | 96.6 | 0.45 |
| " | 7 | Niobium pentoxide | 3.0 | 3.0 | 53.0 | 3.3 | 62.3 | 0.6 | 1.7 | 0.0 | 15.4 | 1.7 | 94.6 | 0.95 |
| " | 8 | Niobium pentoxide | 6.0 | 1.0 | 54.1 | 4.0 | 62.8 | 0.1 | 2.8 | 0.0 | 17.4 | 2.8 | 95.9 | 0.16 |
| " | 9 | Niobium pentoxide | 3.0 | 3.0 | 69.6 | 5.5 | 52.9 | 0.3 | 4.2 | 0.0 | 22.2 | 6.0 | 92.2 | 0.56 |
| " | 10 | Niobium pentoxide | 3.0 | 2.0 | 65.2 | 3.3 | 55.8 | 4.0 | 3.1 | 0.0 | 20.2 | 4.4 | 91.2 | 6.69 |
| " | 11 | Niobic acid | 3.0 | 3.0 | 53.3 | 3.5 | 66.0 | 0.6 | 1.8 | 0.0 | 16.3 | 1.8 | 97.4 | 0.90 |
| Comparative Example | 6 | Aluminum phosphate | 3.0 | 3.0 | 30.0 | 3.7 | 73.5 | 20.1 | 1.1 | 0.1 | 2.3 | 0.0 | 85.7 | 21.5 |
| Comparative Example | 7 | Lanthanum phosphate | 3.0 | 3.0 | 26.8 | 1.8 | 75.1 | 10.4 | 0.8 | 0.0 | 6.6 | 0.0 | 89.4 | 12.2 |
| Comparative Example | 8 | Silica | 12.0 | 6.3 | 28.8 | 3.9 | 51.6 | 27.4 | 1.9 | 0.0 | 5.1 | 0.0 | 88.4 | 34.7 |

EXAMPLES 12 THROUGH 14

The same reactor as used in Example 1 was charged with 90 g of EDA, 60 g of MEA and 4.5 g of a calcined catalyst. The temperature of the charged starting material mixture was elevated to 290° to 305° C. and reaction was carried out at this elevated temperature. After termination of the reaction, the reaction liquid was cooled and the composition of the cooled reaction liquid was analyzed by the gas chromatography. The results are shown in Table 3. The reaction liquid was allowed to stand, and the quantitative analysis of dissolved niobium in the supernatant was carried out by using an inductive coupled plasma emission analysis apparatus (ICP). Niobium was not detected at all.

Niobium oxide (supplied by CBMM Co.) used in Examples 12 and 13 was a powdery catalyst heat-treated at 150° C. for 16 hours, and niobium oxide (supplied by CBMM Co.) used in Example 14 was a powdery catalyst calcined at 350° C. for 16 hours.

TABLE 4

| | Reaction Temperature (°C.) | Reaction Time (hrs) | Conversion of MEA (%) |
|---|---|---|---|
| Example 15 | 310 | 3.0 | 77.9 |
| Example 16 | 250 | 5.0 | 12.6 |
| Example 17 | 200 | 15.0 | 5.2 |
| Comparative Example 9 | 250 | 5.0 | 0.0 |

EXAMPLES 18 THROUGH 20

The same reactor as used in Example 6 was charged with 60 g of EDA, 30 g of MEA and a catalyst shown in Table 5, and the reaction was carried out. After termination of the reaction, the reaction liquid was cooled and the composition of the reaction liquid was analyzed by the gas chromatography. The results are shown in Table 5.

EXAMPLES 21 THROUGH 26

TABLE 3

| | | Catalyst | Reaction temperature (°C.) | Reaction time (hrs) | Conversion of MEA (%) | Reaction products (% by weight) | | | | | | | TETA non-cyclic percentage (%) |
|---|---|---|---|---|---|---|---|---|---|---|---|---|---|
| | | | | | | PIP | DETA | AEEA | HEP | TETA | TEPA | PEHA | |
| Example | 12 | Niobium pentoxide | 290 | 5.0 | 46 | 3.5 | 46.1 | 4.0 | 0.0 | 19.5 | 5.0 | 3.1 | 88 |
| " | 13 | " | 300 | 2.5 | 56 | 4.1 | 41.5 | 3.6 | 0.0 | 22.0 | 6.4 | 3.5 | 87 |
| " | 14 | " | 305 | 1.5 | 54 | 3.9 | 42.0 | 3.5 | 0.0 | 21.9 | 6.7 | 3.4 | 87 |

EXAMPLES 15 through 17 AND COMPARATIVE EXAMPLE 9

The same reactor as used in Example 6 was charged with 60 g of EDA, 30 g of MEA and 3.0 g of niobium pentoxide (supplied by CBMM Co.) calcined at 400° C. for 2 hours in dry air and the reaction was carried out. After termination of the reaction, the reaction liquid was cooled and the composition of the reaction liquid was analyzed according to the gas chromatography and The same reactor as used in Example 6 was charged with starting materials shown in Table 6. Niobium pentoxide (supplied by CBMM Co.) calcined at 400° C. for 2 hours in dry air was added to the charged starting materials and the reaction was carried out. After termination of the reaction, the reaction liquid was cooled and the composition of the reaction liquid was analyzed by the gas chromatography. The results are shown in Table 6.

TABLE 5

|  |  | Catalyst | Amount of catalyst (g) | Reaction temperature (°C.) | Reaction time (hrs) | Reaction products (% by weight) DETA | AEEA | Hydroxyl group content (%) |
|---|---|---|---|---|---|---|---|---|
| Example | 18 | Potassium niobate | 3.0 | 300 | 5.0 | 63.3 | 0.3 | 0.47 |
| " | 19 | Barium niobate | 3.0 | 300 | 5.0 | 63.3 | 0.7 | 1.09 |
| " | 20 | Lead niobate | 3.0 | 300 | 5.0 | 53.3 | 0.5 | 0.93 |

TABLE 6

|  |  | Starting materials (g) | | | Reaction temperature (°C.) | Reaction time (hrs) | Conversion of MEA (%) | Reaction products (% by weight) | | | | | | |
|---|---|---|---|---|---|---|---|---|---|---|---|---|---|---|
|  |  | EDA | MEA | NH$_3$ |  |  |  | EDA | PIP | DETA | AEEA | AEP | HEP | TETA | TEPA |
| Example | 21 | 30.0 | 60.0 | — | 300 | 1.0 | 40.2 | — | 4.8 | 31.2 | 27.8 | 3.6 | 0.3 | 19.6 | 4.8 |
| " | 22 | 45.0 | 45.0 | — | 300 | 1.0 | 41.2 | — | 3.3 | 53.3 | 9.6 | 2.1 | 0.0 | 18.4 | 4.2 |
| " | 23 | 72.0 | 18.0 | — | 300 | 1.0 | 52.8 | — | 2.3 | 79.1 | 1.1 | 0.9 | 0.0 | 12.6 | 0.0 |
| " | 24 | 60.0 | 30.0 | 32.7 | 280 | 5.0 | 42.5 | — | 3.5 | 72.3 | 3.6 | 1.5 | 0.0 | 9.2 | 0.0 |
| " | 25 | 30.1 | 15.0 | 54.0 | 280 | 6.0 | 47.8 | — | 3.8 | 63.0 | 4.0 | 1.8 | 0.0 | 16.7 | 1.5 |
| " | 26 | — | 15.2 | 54.7 | 280 | 3.0 | 33.9 | 29.7 | 5.0 | 9.3 | 26.4 | 5.2 | 0.0 | 7.3 | 2.1 |

EXAMPLE 27

The same reaction vessel as used in Example 1 was charged with 40 g of NH$_3$, 71 g of MEA and 3.5 g of niobium pentoxide (supplied by CBMM Co. heat-treated at 150° C. for 16 hours. The temperature of the charged starting material mixture was elevated to 300° C. and the reaction was carried out for 3 hours at this temperature. The reaction pressure was 155 kg/cm$^2$. After termination of the reaction, the reaction liquid was cooled and the composition of the reaction liquid was analyzed by the gas chromatography. The conversion of MEA was 50%, and the reaction product comprised 31.5% by weight of EDA, 4.7% by weight of PIP, 13.5% by weight of DETA, 6.0% by weight of AEEA, 6.8% by weight of AEP, 1.3% by weight of HEP, 12.8% by weight of TETA and 11.4% by weight of TEPA.

EXAMPLE 28

A stainless steel continuous reaction apparatus having a capacity of 100 ml, which was capable of being charged with a catalyst, was charged with small granules of a niobium pentoxide catalyst calcined at 300° C. for 16 hours. A starting material mixture comprising MEA and EDA at a molar ratio of ½ was continuously supplied into the reaction apparatus. The reaction temperature was maintained at 300° C. The reaction product was periodically sampled and the composition was analyzed by the gas chromatography. Supply of the starting material mixture was performed at a constant rate by a high-pressure metering pump. The results obtained after 5 hours and 100 hours are shown in Table 7. The change of the conversion of MEA with the lapse of time was not observed, and almost no change was observed in the distribution of products.

EXAMPLE 29

The same reactor as used in Example 6 was charged with 60 g of DETA, 30 g of AEEA and 3.0 g of niobium pentoxide (supplied by CBMM Co.) calcined at 400° C. for 2 hours in dry air, and the reaction was carried out at 300° C. for 2 hours. After termination of the reaction, the reaction liquid was cooled and the composition of the reaction liquid was analyzed by the gas chromatography. The conversion of AEEA was 93.2%, and the reaction product comprised 12.7% by weight of PIP, 4.0% by weight of AEP, 17.0% by weight of TETA, 25.4% by weight of TEPA and 6.4% by weight of PEHA.

EXAMPLE 30

The same reactor as used in Example 6 was charged with 72 g of 1,3-propylenediamine and 18 g of 3-amino-1propanol, and 3.0 g of niobium pentoxide (supplied by CBMM Co.) calcined at 400° C. for 2 hours in dry air was added and the reaction was carried out at 300° C. for 34 minutes. After termination of the reaction, the reaction liquid was cooled and the composition of the reaction liquid was analyzed by the gas chromatography. It was found that the reaction product comprised 55.4% by weight of dipropylenetriamine, 13.2% by weight of tripropylenetetramine and 1.4% by weight of tetrapropylenepentamine.

We claim:

1. A process for preparing an elkyleneamine having an increased number of alkylene units from a starting material selected from the group consisting of ammonia and aklyleneamines and wherein the alkyleneamine starting material is selected from the group consisting of: compounds represented by the following formula (I):

TABLE 7

| Reaction time (hrs) | Conversion of MEA (%) | Reaction products (% by weight) | | | | | | | | TETA non-cyclic percentage (%) |
|---|---|---|---|---|---|---|---|---|---|---|
|  |  | PIP | DETA | AEEA | AEP | HEP | TETA | TEPA | PEHA |  |
| 5 | 60 | 3.1 | 54.5 | 0.1 | 2.4 | 0 | 16.9 | 3.3 | 1.1 | 92 |
| 100 | 61 | 3.0 | 54.9 | 0.1 | 2.4 | 0 | 17.3 | 3.4 | 1.0 | 92 |

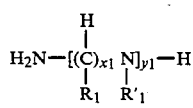

(I)

wherein $X_1$ is a number from 2 to 6, $Y_1$ is a number from 1 to 6, $R_1$ represents a hydrogen atom or an alkyl group having 1 to 4 carbon atoms, and $R'$, represents a group represented by the following formula (1):

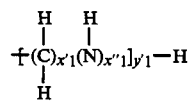

(1)

wherein $X'_1$, is a number from 1 to 6, $X''_1$ is 0 or 1 and $Y'_1$ is a number from 0 to 4, and compounds represented by the following formula (II):

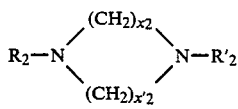

(II)

wherein $X_2$ and $X'_2$ are numbers from 2 to 6, and $R_2$ and $R'_2$ represent a group represented by the following formula (2):

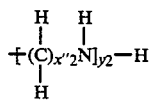

(2)

wherein $X''_2$ is a number from 2 to 6 and $Y_2$ is a number from 0 to 5; and further wherein the starting material is reacted with an alkanolamine in the presence of a niobium-containing substance selected from the group consisting of niobium oxides, niobic acid salts, fluroniobic acid salts, niobium fluorides, niobium chlorides, niobium bromides, niobium iodides, niobium oxyhalides, niobium alkoxides, and niobium salts of organic acids.

2. A process according to claim 1, wherein the niobium-containing substance is niobium pentoxide or a niobic acid salt.

3. A process according to claim 1, wherein the alkyleneamine used as a starting material is an ethyleneamine or a propyleneamine.

4. A process according to claim 4, wherein the ethyleneamine is ehylenediamine or diethylenetriamine.

5. A process according to claim 1, wherein the propyleneamine is 1,3-propylenediamine.

6. A process according to claim 1, wherein the alkanolamine is selected from the group consisting of:
compounds represented by the following formula (III):

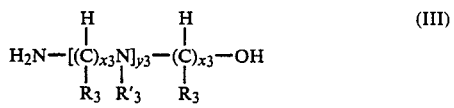

(III)

wherein $x_3$ is a number of from 2 to 6, $y_3$ is a number of from 0 to 5, $R_3$ represents a hydrogen atom or an alkyl group having 1 to 4 carbon atoms, and $R'_3$ is a group represented by the following formula (3):

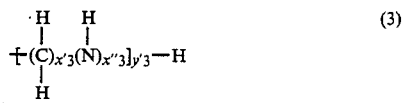

(3)

wherein $x'_3$ is a number of from 1 to 6, $x''_3$ is 0 or 1 and $y_3$ is a number of from 0 to 4, and compounds represented by the following formula (IV):

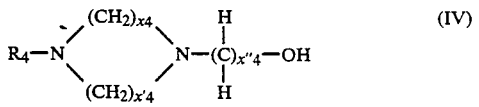

(IV)

wherein $x_4$, $x'_4$ and $x''_4$ are numbers of from 2 to 6 and $R_4$ represents a group represented by the following formula (4):

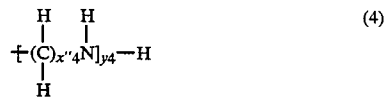

(4)

wherein $x''_4$ is a number of from 2 to 6 and $y_4$ is a number of from 0 to 4.

7. A process according to claim 1, wherein the alkanolamine is an ethanolamine or a propanolamine.

8. A process according to claim 7, wherein the ethanolamine is monoethanolamine or N-(2-aminoethyl) ethanolamine.

9. A process according to claim 7, wherein the propanolamine is 3-amino-1-propanol.

* * * * *

UNITED STATES PATENT AND TRADEMARK OFFICE
CERTIFICATE OF CORRECTION

PATENT NO. : 4,906,782

DATED : March 6, 1990

INVENTOR(S) : Hara et al.

It is certified that error appears in the above-identified patent and that said Letters Patent is hereby corrected as shown below:  ON THE TITLE PAGE:

Abstract, line 2, change "miobium" to --niobium--.

Signed and Sealed this

Thirtieth Day of November, 1993

*Attest:*

BRUCE LEHMAN

*Attesting Officer*  *Commissioner of Patents and Trademarks*